United States Patent
Banerjee et al.

(10) Patent No.: US 9,393,276 B2
(45) Date of Patent: Jul. 19, 2016

(54) EDIBLE COMPOSITION

(71) Applicant: Conopco,Inc., Englewood Cliffs, NJ (US)

(72) Inventors: Gautam Banerjee, Bangalore (IN); Vinitha Kadamkode, Bangalore (IN); Ramitha Kalathil, Bangalore (IN); Suman Majumder, West Bengal (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/649,629

(22) PCT Filed: Nov. 18, 2013

(86) PCT No.: PCT/EP2013/074069
§ 371 (c)(1),
(2) Date: Jun. 4, 2015

(87) PCT Pub. No.: WO2014/090512
PCT Pub. Date: Jun. 19, 2014

(65) Prior Publication Data
US 2015/0306161 A1    Oct. 29, 2015

(30) Foreign Application Priority Data

Dec. 13, 2012 (EP) .................................... 12196859

(51) Int. Cl.
| | | |
|---|---|---|
| A61K 36/00 | (2006.01) | |
| A61K 36/28 | (2006.01) | |
| A23L 1/30 | (2006.01) | |
| A23L 1/39 | (2006.01) | |
| A61K 36/82 | (2006.01) | |
| A61K 36/185 | (2006.01) | |
| A61K 31/522 | (2006.01) | |

(52) U.S. Cl.
CPC ............... *A61K 36/28* (2013.01); *A23L 1/3002* (2013.01); *A23L 1/39* (2013.01); *A61K 31/522* (2013.01); *A61K 36/185* (2013.01); *A61K 36/82* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2007/0219146 A1* | 9/2007 | Bhaskaran et al. ............. | 514/27 |
| 2011/0274680 A1 | 11/2011 | Mazed et al. | |
| 2012/0094942 A1 | 4/2012 | Baron et al. | |

FOREIGN PATENT DOCUMENTS

| | | |
|---|---|---|
| CN | 102578337 A | 7/2012 |
| CN | 102579810 A | 7/2012 |
| EP | 0920870 | 6/1999 |
| JP | 2010013400 | 1/2010 |
| WO | WO2007091151 | 8/2007 |
| WO | WO2007101349 | 9/2007 |
| WO | WO2008118011 | 10/2008 |
| WO | WO2010100652 A1 | 10/2010 |

OTHER PUBLICATIONS

Ajani, Evaluation of antidiabetic effect of methanolic extract of inula racemosa root in rats. Pharmacologyonline, (Sep./Dec. 2009) vol. 3, pp. 118-129.*
Saldana, Extraction of methylxanthines from guarana seeds, mate leaves, and cocoa beans using supercritical carbon dioxide and ethanol. Journal of agricultural and food chemistry, (Aug. 14, 2002) vol. 50, No. 17, pp. 4820-4826.*
Tripathi et al, screening of hypoglycaemic action in certain indigenous drugs, J. Res., Indian Med. Yoga & Homoeop 14: 159-169.*
Alan L. Miller, N.D., Botanical influences on cardiovascular disease, Alternative Medicine Review, 1998, pp. 421-431; XP002996497, vol. 3 No. 6.
Chandra et al., Role of Apoptosis in Pacreatic B-Cell Death in Diabetes, Diabetes, 2001, 1-4, 50, 1.
Gregory S. Kelly, ND, Insulin Resistance: Lifestyle 1-15 and Nutritional Intervention, Alternative Medicine Review, 2000, pp. 109-132; XP008007150, vol. 5 No. 2.
IPRP2 in PCTEP2013074069, Apr. 8, 2015.
IPRP2 in PCTEP2013074735, Apr. 8, 2015.
Search Report in EP12196859, Jun. 13, 2013.
Search Report in PCTEP2013074069, Jan. 2, 2014.
Search Report in PCTEP2013074735, Jan. 7, 2014.
Vincent et al., Glucolipotoxicity: Fuel Excess and B-Cell Dysfuntion, Endocrine Reviews, 2008, 351-366, 29, 3.
Written Opinion 1 in PCTEP2013074735, Jan. 7, 2014.
Written Opinion in PCT/EP2013/074069, Jan. 19, 2015.
Co-Pending Application: Applicant: Balaram Signgh et al., Filed: Jun. 4, 2015.

* cited by examiner
(Continued)

*Primary Examiner* — Qiuwen Mi
(74) *Attorney, Agent, or Firm* — Greenberg Traurig, LLP

(57) ABSTRACT

The present invention provides relates to an edible composition for anti-diabetic benefit. Diabetes is one of the major and commonly occurring health problems in today's world. Pharmaceuticals companies are very active in this field to develop new medicines for preventing and controlling diabetes. There are several medicines available in the market for the treatment of type 2 diabetes. There are also prior arts which describes composition for the prevention of glucose intolerance and/or diabetes. We have found that though prior that discloses compositions for prevention of glucose intolerance and/or diabetes, it is not that effective for preventing diabetes. The present inventors while working extensively for providing an edible composition for preventing diabetes have surprisingly found that a particular combination of *Inula racemosa* and theobromine is effective for controlling and/or preventive diabetes thereby satisfying one or more of the aforesaid objects.

11 Claims, No Drawings

EDIBLE COMPOSITION

FIELD OF THE INVENTION

The present invention relates to an edible composition. Most particularly the present invention relates to an edible composition for anti-diabetic benefit.

BACKGROUND OF THE INVENTION

Diabetes is one of the major and commonly occurring health problems in today's world. Some people inherited diabetes from their parents (type 1) and some of them acquired it because of their unhealthy life style and metabolic disorder (type 2). Whether it is type 1 or type 2, in the long term diabetes can be proved to be a life threatening disease in absence of any early actions to prevent it.

Human pancreas contains β-cell which is responsible for release of a hormone named as insulin thereby controls blood glucose level. Dysfunction of this β-cell is common for both type 1 and type 2 diabetes. In the case of type 2 diabetes insulin secretion by β-cell gets reduced thereby increases blood glucose level (Section 2: β-cell Apoptosis, "Role of Apoptosis in Pancreatic β-cell Death in Diabetes", Joya Chandra et. al., *DIABETES*, VOL. 50, *SUPPLEMENT* 1, FEBRUARY 2001). Higher blood glucose level with the availability of higher level of free fatty acids (lipids) induced β-cell toxicity and ultimately results in death of β-cell (Glucolipotoxicity: Fuel Excess and β-cell Dysfunction, Vincent et. al, *Endocrine Reviews*, May 2008, 29(3): 351-366).

Pharmaceuticals companies are very active in this field to develop new medicines for preventing and controlling diabetes. There are several medicines available in the market for the treatment of type 2 diabetes.

One of the problem with diabetes is that people generally do not consider this as a serious disease as because there are no immediate visual effects of this disease. Therefore most of the people do not take any action to prevent it. Another problem in general with medicine is that people takes medicine only when they are not well. Taking medicine everyday generally has some negative psychological effect.

There are prior arts which describes composition for the prevention of glucose intolerance and/or diabetes.

WO 2007/091151 (Indus Biotech private limited, 2007) relates to a synergistic pharmaceutical and/or neutraceutical flavanoid composition for management of Diabetes Mellitus, said composition comprising polyphenol of concentration ranging between 85 to 95% (w/w) GAE theobromine of concentration ranging between 1 to 5% (w/w), and moisture content ranging between 0.5 to 10% (v/w).

WO 2010/100652 (Anurag Sharma, 2010) discloses an herbal formulation for the prevention and management of various CHD risk factors including vascular inflammatory process responsible for cardiovascular events comprising a hydro-alcoholic extraction of *Commiphora mukul, Terminalia arjuna, Inula racemosa* and *Hippophae rhamonoides* with or without known additives.

WO2007/101349 (Chaudhuri, 2007) discloses a composition and method for promoting weight loss through the mutual and simultaneously to promotion lipolysis, the expenditure of energy stored in the body as fat, the inhibition of lipolysis as well as affording the body of an individual protection from reactive oxygen species resulting from the beta-oxidation of fats. The composition comprises at least a lipolytic substance, a thermogenic substance, a substance to inhibit the reformation of triglycerides in the bodily tissues of an individual and an antioxidant. *Inula racemosa* and green tea combination at very low levels or theobromine, alone along with a number of other herbs and chemical compounds is mentioned in a dietary supplement composition to reduce body fat mass or increase individual's natural adipose metabolism. It does not disclose edible food compositions comprising selective amounts of *Inula racemosa* and theobromine to obtain synergistic benefits for allowing normal functioning of the β-cell by controlling and/or preventing diabetes.

We have found that though prior that discloses compositions for prevention of glucose intolerance and/or diabetes, it is not that effective for preventing diabetes.

Therefore there is a need to provide an edible composition which allows normal functioning of the β-cell without taking any medicine and in turn without any negative psychological effect.

OBJECTS OF THE INVENTION

It is therefore an object of the present invention to provide an edible composition for preventing diabetes.

It is another object of the present invention to provide an edible composition which allows normal functioning of the β-cell.

It is yet another object of the present invention to provide for a suitable alternative for controlling and preventing diabetes.

The present inventors while working extensively for providing an edible composition for preventing diabetes have surprisingly found that a particular combination of *Inula racemosa* and theobromine is effective for controlling and/or preventive diabetes thereby satisfying one or more of the aforesaid objects.

SUMMARY OF THE INVENTION

According to a first aspect of the present invention there is provided an edible composition comprising:
  a. 0.1 to 10% by weight of extract of *Inula racemosa*; and
  b. 0.01 to 10% by weight of theobromine.

According to the second aspect of the present invention there is provided a process of producing an edible composition comprising the steps of mixing and/or blending 0.1 to 10% by weight of extract of *Inula racemosa* and 0.01 to 10% by weight of theobromine with the other ingredients to obtain the edible composition.

Any feature of one aspect of the present invention may be utilized in any other aspect of the invention. The word "comprising" is intended to mean "including" but not necessarily "consisting of" or "composed of." In other words, the listed steps or options need not be exhaustive. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides an edible composition comprising:
  a. 0.1 to 10% by weight of extract of *Inula racemosa*; and
  b. 0.01 to 10% by weight of theobromine.

The term edible composition preferably means a composition which is ingestible by human being.

The edible composition preferably comprises 1 to 10%, more preferably 3 to 10% and most preferably 5 to 10% by weight of extract of *Inula racemosa*.

*Inula racemosa* is a species of an ornamental plant of the Asteraceae family. *Inula racemosa* grows in the temperate and alpine western Himalayas, and it is common in Kashmir, and also known as "Pushkarmool". "Extract of *Inula racemosa*" herein is to be understood as a composition obtainable by extracting roots of such plants or preferably parts of such roots with liquid and preferably water Herein, "extract of *Inula racemosa*" is the same as "*Inula racemosa* extract". All the above mentioned percentage is on solid weight basis of the composition. If the composition is having high percentage of water then the percentage of the extract of *Inula racemosa* as mentioned above has to construe accordingly.

The edible composition also preferably comprises 0.1 to 10%, more preferably 0.1 to 8% and furthermore preferably 0.1 to 5% by weight of theobromine.

"Theobromine" herein relates to the molecular structure as set out below, and is chemically known as 2,6-dihydroxy-3,7-dimethylpurine or 3,7-dimethylxanthine (chemical formula: $C_7H_8N_4O_2$, Mw=180.16), including the edible salts thereof.

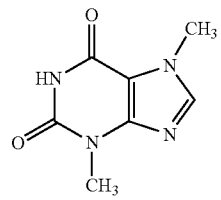

Theobromine is a class of bitter alkaloid molecule naturally occurs in many of the plant species. The preferred source of theobromine is from cocoa plant.

Preferably in the composition of the present invention, the ratio of extract of *Inula racemosa* to theobromine is in the range of 25:1 to 1:25, more preferably in the range of 10:1 to 1:10 and further more preferably in the range of 5:1 to 1:5 and most preferably in the range of 2:1 to 1:2.

Though the edible composition of the present invention is not limited to any particular edible composition but the preferred composition of the present invention is in the form of a liquid such as a soup or a beverage, a spread, a dressing, a dessert or bread.

The most preferred beverage is tea based beverage.

The term tea based beverage as herein referred to preferably include black tea based beverages, green tea based beverage and oolong tea based beverages. The preferable format may be liquid tea drink, ready-to-drink tea, tea juice etc. both hot and/or cold brew.

The edible composition of the present invention may also be in the form of a solid or powdered food supplement.

The present invention also provides a process of producing an edible composition comprising the steps of mixing and/or blending 0.1 to 10% by weight of extract of *Inula racemosa* and 0.01 to 10% by weight of theobromine with the other ingredients to obtain the edible composition.

The term "other ingredients" as mentioned above means the compositional ingredients needed for making a targeted edible product e.g. in case of making a soup composition (targeted edible product) the term "other ingredients" preferably are starch, salt, sugar, yeast extract, fat powder, vegetable pieces, flavour, colour etc.

To make the edible composition of the present invention, the *Inula racemosa* extract may be prepared by extracting (boiling) the roots of *Inula racemosa* with water at a temperature in the range of 70 to 100° C. for 2-6 hours followed by cooling. After that the solution is filtered and concentrated. The concentration stage preferably carried out in a rotary evaporator.

Alternately, commercially available (if available) *Inula racemosa* water extract powder may also be used.

The composition of the present invention has been primarily developed for preventing and controlling diabetes and more particularly type 2 diabetes.

The present invention provides the use of a composition for anti-diabetic benefit.

The present invention provides the use of a composition for the treatment of type 2 diabetes.

The present invention provides the use of a composition for normal functioning of the β-cell.

The invention will now be demonstrated with the help of examples, which are for the purpose of illustration, and in no way limit the scope of the invention.

EXAMPLES

Preparation of Extract of *Inula racemosa*

*Inula racemosa* extract was prepared by using the following procedure:

The *Inula racemosa* (pushkarmool) plant was bought from the local (Bangalore, India) market. This was available as a stem size of ~3-6 cm which was a combination of roots and stems of pushkarmool. The dried *Inula racemosa* powder was then prepared by a pulverizer (cutting mill, Retsch SM 100) attached with a 200 μm size sieve.

The extract of the *Inula racemosa* was prepared from dried *Inula racemosa* powder. 100 g of dry *Inula racemosa* root powder was soaked in 800 mL of water for ~14 hours and then boiled at 80° C. for 4 hours. It was then cooled down to ~35° C. followed by filtering the solution to get a clear solution. The solution was then concentrated to dryness (moisture content of ~3%) using rotary evaporator (Heidolph Laborota 4002). This extract was used for the other experiments as described below.

Invitro-β Cell Protection Assay to Determine Anti-Diabetic Benefit

Before starting the experiment it was needed to determine the cytotoxic dose for the *Inula racemosa* extract and theobromine. The cytotoxicity of both materials was determined as follows by Neutral red assay:

The Rat Insulinoma cell lines (RIN-5F, ATCC (USA)) was plated at a density of $3.5 \times 10^4$ cells/well (Volume 100 μL) in a 96 well plate (NEST Biotechnology Co. Ltd, Cat No 701001) and placed it in an incubator (Thermo Scientific, Model 3111; conditions: 5% CO2, at 37° C.) for 24 hours. After the incubation 10 μL of *Inula racemosa* water extract (at different concentration e.g. 10%, 1%, 0.1%, 0.01%, 0.001%, 0.0001% and 0.00001%) and 10 μL of theobromine solution (at different concentration e.g. 10%, 1%, 0.1%, 0.01%, 0.001%, 0.0001% and 0.00001%) were added to the culture and incubated for 24 hours in the same incubator. As a control in some wells there was no addition of either *Inula racemosa* or theobromine (only medium and cells).

After 24 hours the medium was removed and 100 μL of neutral red solution was added to the culture and incubated for 4 hours in the same incubator under the same condition. The neutral red solution was prepared by adding 4 µg of neutral red dye (Sigma, Cat. No. N-2880) in 100 µL of phenol red free RPMI media (Sigma, Cat. No. R7509).

After 4 hrs the neutral red medium was removed by aspiration using a micropipette and cells were washed with 100 µL/well of PBS (Phosphate Buffered Saline) solution to remove the excess stain. The PBS solution was prepared by adding 400 µg of Sodium Chloride (NaCl), 10 ng of Potassium Chloride (KCl-SRL Cat No: 1644133), 57.5 ng of Sodium Phosphate Dibasic ($Na_2HPO_4$, SRL Cat No: 1944143), 10 µg of Potassium Phosphate Dibasic ($KH_2PO_4$, SRL Cat No: 1649201) in 100 µL of autoclaved distilled water (Neutral red stain binds only to live cells).

The bound stain was extracted out from the cells by adding 150 µL of desorption solution and dissolved the dye completely. The desorption solution was made by mixing 96% ethanol, deionized water and glacial acetic acid in the ratio of 50:49:1. The absorbance of the stain extracted out from the cells was measured at 540 nm in a microwell plate reader (BIO-RAD LAB INDIA, Model No. 680).

The percentage of live cells was calculated using the below mentioned formula:

$$\frac{OD \text{ of the test ingredient treated cells}}{OD \text{ of the control cells}} \times 100$$

If the percentage of live cells in *Inula racemosa* or theobromine treated cells were ≥95% with respect to control, it was considered to be non cytotoxic and then those concentrations of *Inula racemosa* or theobromine were used for further experiments. It was found the non-cytotoxic concentration is 0.001% or below.

a) Cell Culture:

Rat Insulinoma cell lines (RIN-5F) were procured from ATCC (USA). RPMI 1640 medium (Cat No: R6504) are also procured from Sigma. This RPMI 1640 medium contains 2 g/L of glucose supplemented with 25 mM HEPES (4-(2-hydroxyethyl)-1-piperazineethanesulfonic acid, SRL Cat No: 084023C).

After that a complete medium was prepared by adding 100 µL of 100 mM Sodium pyruvate (Sigma, Cat No: P5280) and 10% (vv) in 100 mL of RPMI 1640.

100 µL/well of complete medium with the added Rat Insulinoma cell (RIN-5F, ATCC (USA)) was plated in a 96 well flat bottom plate (NEST Biotechnology Co. Ltd, Cat No 701001) so that the cell concentration is maintained at a level of $3.5 \times 10^4$ cells/well. This plate was then introduced in an incubator (Thermo Scientific, Model 3111; conditions: 5% CO2, at 37° C.) for 24 hours.

b) Preparation of Palmitate-BSA (Bovine Serum Albumin) Complex:

Preparation of BSA Solution:
1. 2.267 g of ultra Fatty Acid Free BSA (Roche applied sciences, Cat No: 03117405001) was added to 100 mL of 150 mM NaCl and stirred constantly at a maintained temperature of ~37° C. (did not go beyond ~40° C.) for about 30 minutes until BSA dissolved completely.
2. After that this solution was filtered with a syringe filter of pore size of 0.22 µm (Millipore®, Cat no: SLGP033RS).
3. 50 mL of the filtered solution was taken in a pre-warmed 250 mL beaker and covered it with parafilm.
4. A 1 L half filled (~500 mL) beaker was placed in a water bath maintained at a temperature of ~37° C. The 250 mL beaker containing the solution (as described in step 3) was placed in the 1 L half filled beaker.
5. The remaining filtered BSA solution with was diluted with 50 mL of 150 mM NaCl solution, to make 0.17 mM of BSA solution.
6. This solution was aliquoted into 4 mL glass vials and freezed at −20° C. for later use in the assay as vehicle control.

Preparing Palmitate Solution:
1. 30.6 mg of Sodium Palmitate (Sigma, Cat. No P9767) was added to 44 mL of 150 mM NaCl solution in a flask.
2. This flask was then place in a water bath and heated to ~70° C. while stirring.

Forming Palmitate-BSA Complex:
1. 40 mL of the Palmitate solution as prepared above was added to 50 mL of 0.17 mM of BSA solution as prepared above while stirring at 37° C. in a water bath for about 1 hour. The temperature was maintained between 35° to 40° C. during the experiment.
2. The final volume was adjusted to 100 mL with 150 mM NaCl.
3. The pH was then adjusted to 7.4 with 1N NaOH β-Cell Assay Protocol for Protection Against Gluco-Lipo Toxicity (Diabetes Model):

After 24 hrs the 96 well plate containing RIN-5F cells (as described above) was taken out from the incubator. To evaluate the efficacy of *Inula racemosa* aqueous extract and theobromine and their combinations, the culture was treated with different concentrations (non-cytotoxic) of *Inula racemosa* and theobromine and their combinations as given below in Table 1 along with two control (one with only medium (Control 1) and another with glucose and Palmitate at the same concentration (Control 2)) This plate was then treated with 10 µL/well of 50 mM of glucose (SRL Dextrose Cat No: 0449130) solution and 10 µL/well of Palmitate-BSA complex was added and again incubated (Thermo Scientific, Model 3111; conditions: 5% CO2, at 37° C.) for 18 hrs. After incubation the medium was removed and 100 µL/well of neutral red solution prepared in phenol red free media was added and incubated for 4 hrs in the same incubator. The neutral red solution is prepared as explained above.

After 4 hrs the neutral red medium was removed by aspiration using a micropipette and cells were washed with 100 µL/well of PBS solution (same as prepared above) to remove the excess stain. The bound stain was extracted out from the cells by adding 150 µL of desorption solution (as prepared above) and dissolved the dye completely. The colorimetric reading (absorbance) of the bound stain was read at a wavelength of 540 nm in a microwell plate reader (BIO-RAD LAB INDIA, Model No. 680). The efficacy of the test ingredients were evaluated with respect to the Control 2. The cells treated with only glucose and Palmitate kills about 50% of the cells with respect to the Control 1. If the test ingredients are effective in protecting the cells from high glucose and high fat, the viable cell number increases.

The % change in cell viability with respect to the Control 2 was calculated using the following formula.

$$\left[ \frac{OD \text{ of the test ingredient treated wells} \times 100}{OD \text{ of the Control 2}} \right] - 100$$

The higher the "% change in cell viability" the better the samples are for protecting the β-cell and in turn better for controlling diabetes.

The results are summarized below in Table 1.

TABLE 1

| Example Number | Inula racemosa (wt %) | Theobromine (wt %) | Ratio of Inula racemosa: Theobromine | % change in cell viability |
|---|---|---|---|---|
| A | 0.0001 | — | — | 23 ± 2 |
| B | 0.00002 | — | — | 14 ± 2 |
| C | 0.00001 | — | — | 3 ± 2 |
| D | — | 0.00001 | — | −1 ± 3 |
| E | — | 0.00002 | — | 5 ± 2 |
| 1 | 0.0001 | 0.00001 | 10:1 | 42 ± 13 |
| 2 | 0.00002 | 0.00001 | 2:1 | 36 ± 14 |
| 3 | 0.00001 | 0.00001 | 1:1 | 48 ± 4 |
| 4 | 0.00001 | 0.00002 | 1:2 | 34 ± 9 |

From the above table it is evident that examples (1, 2, 3 and 4) which has combinations of *Inula racemosa* and theobromine in a ratio inside the scope of the present invention provides enhanced (better) "% change in cell viability" than the individual ingredients (Examples A, B, C, D and E) at the same concentration. It is also clear from the above table that the above combinations as provided in Examples 1 to 4, provides synergistic benefit.

Preparation of Edible Compositions:

Soup Composition:

The soup composition was made by mixing the dry ingredient according to the following Table:

TABLE 2

| Ingredient | Wt % |
|---|---|
| Corn Starch | 47 |
| NaCl | 10.5 |
| Sugar (commonly available sucrose) | 12.4 |
| Yeast Extract | 2 |
| Fat Powder (Lecithin) | 4 |
| Liquid Fat (Lecithin) | 2 |
| Dried vegetable pieces | 18.9 |
| Flavour | 2.5 |
| Colour | 0.5 |
| *Inula racemosa* extract | 0.1 |
| Theobromine | 0.1 |

The soup was then prepared using 15 g of the above composition in 100 mL of hot water (~90° C.) and tasted by a group of professional taster. It was found that the addition of *Inula racemosa* extract and theobromine did not alter the taste of the soup. The soup was as delicious as a control soup (without the addition of *Inula racemosa* extract and theobromine).

The invention claimed is:

1. An edible composition comprising:
   a. an extract of *Inula racemosa*; and
   b. theobromine,
   wherein the ratio of *Inula racemosa* to theobromine is from 1:2 to 2:1.

2. A composition as claimed in claim 1 wherein the *Inula racemosa* extract is an extract of *Inula racemosa* root or parts thereof.

3. A composition as claimed in claim 2 wherein the *Inula racemosa* extract is water extract.

4. A composition as claimed in claim 1 wherein the source of theobromine is a plant.

5. A composition as claimed in claim 4 wherein the plant is cocoa.

6. A composition as claimed in claim 1 in the form of a liquid, a spread, a dressing, a dessert or bread.

7. A composition as claimed is claim 6 wherein the liquid is a tea based beverage.

8. A composition as claimed in claim 1 in the form of a solid or powdered food supplement.

9. A composition as claimed in claim 1 for use in treating diabetes.

10. A composition as claimed in claim 1 for use in treating type 2 diabetes.

11. A composition as claimed in claim 1 for use in maintaining normal functioning of the β-cell.

* * * * *